US 6,524,866 B1

(12) United States Patent
Hughes et al.

(10) Patent No.: US 6,524,866 B1
(45) Date of Patent: Feb. 25, 2003

(54) CAPILLARY ELECTROPHORETIC METHOD TO DETECT TARGET-BINDING LIGANDS AND TO DETERMINE THEIR RELATIVE AFFINITIES

(75) Inventors: Dallas E. Hughes, Westboro, MA (US); James L. Waters, Framingham, MA (US); Yuriy M. Dunayevskiy, Natick, MA (US)

(73) Assignee: Cetek Corporation, Marlborough, MA (US)

( * ) Notice: Subject to any disclaimer, the term of this patent is extended or adjusted under 35 U.S.C. 154(b) by 0 days.

(21) Appl. No.: 09/582,065

(22) PCT Filed: Dec. 23, 1998

(86) PCT No.: PCT/US98/27463

§ 371 (c)(1),
(2), (4) Date: Jun. 21, 2000

(87) PCT Pub. No.: WO99/34203

PCT Pub. Date: Jul. 8, 1999

Related U.S. Application Data

(60) Provisional application No. 60/068,781, filed on Dec. 24, 1997.

(51) Int. Cl.[7] .................. G01N 27/26; G01N 27/447; G01N 33/53; G01N 33/543; G01N 33/561

(52) U.S. Cl. .................. 436/516; 204/180.1; 204/451; 204/452; 204/453; 204/299; 204/407; 204/600; 204/601; 204/602; 204/603; 204/604; 204/605; 204/606; 204/607; 204/608; 204/610; 204/612; 204/615; 204/616; 204/617; 204/618; 204/621; 435/4; 435/5; 435/6; 435/7.1; 435/7.2; 435/7.8; 435/7.9; 435/7.92; 356/344; 210/198.2; 436/514; 436/515; 436/536; 436/538; 436/540

(58) Field of Search .................. 204/451, 452, 204/453, 180.1, 299, 407, 600–621; 435/7.1, 6, 7.8, 7.92, 4, 5, 7.2; 356/344; 210/198.2; 436/514, 515, 536, 516, 6, 538, 540

(56) References Cited

U.S. PATENT DOCUMENTS

| 4,906,344 | A | * | 3/1990 | Hjerten ............... 264/182.8 |
| 5,114,551 | A | * | 5/1992 | Hjerten et al. .......... 204/180.1 |
| 5,228,960 | A | * | 7/1993 | Liu et al. ............. 204/182.8 |
| 5,536,382 | A | | 7/1996 | Sunzeri ................ 204/451 |
| 5,699,157 | A | * | 12/1997 | Parce ................. 356/344 |
| 5,783,397 | A | * | 7/1998 | Hughes et al. .......... 435/7.1 |
| 6,299,747 | B1 | * | 10/2001 | Dunayevskiy et al. .... 204/451 |

FOREIGN PATENT DOCUMENTS

| EP | 0 572 023 A2 | 5/1993 | ......... G01N/27/447 |
| WO | WO 94/03631 | 2/1994 | ......... C12Q/1/06 |
| WO | WO 94 09185 A | 4/1994 | |
| WO | WO 96/04547 | 2/1996 | ......... G01N/27/00 |
| WO | WO 9635946 | * 11/1996 | ......... 27/447 |
| WO | WO 97 22000 A | 6/1997 | |

OTHER PUBLICATIONS

Chu J. Am. Chem. Soc. 1996 118 7827–7835.*
Wagner et al J Med. Chem. 1992 35 2915–2917.*
Smith et al Comput Appl. Biosci. (1990) 6 (2).*

* cited by examiner

*Primary Examiner*—Long V. Le
*Assistant Examiner*—Kartic Padmanabhan
(74) *Attorney, Agent, or Firm*—Weingarten, Schurgin, Gagnebin & Lebovici LLP

(57) ABSTRACT

The invention relates to capillary electrophoretic methods for detecting ligands or hit compounds that can bind to a selected target at or above a selected binding strength. The method allows one to rank various ligands based on their relative affinity, i.e., the relative stability of the target/ligand complex during capillary electrophoresis under selected conditions. The method also enables selective detection of strong-to-moderate binding hit compounds, even in the presence of high concentrations of weaker, competitive hit compounds.

28 Claims, 7 Drawing Sheets

Single Detector, Multiple Runs

Step (1) : Provide target
Step (2) : Provide sample possibly having hit compound
Step (3) : Mix target and sample
Step (4) : Inject target/sample plug into CE having single detector:

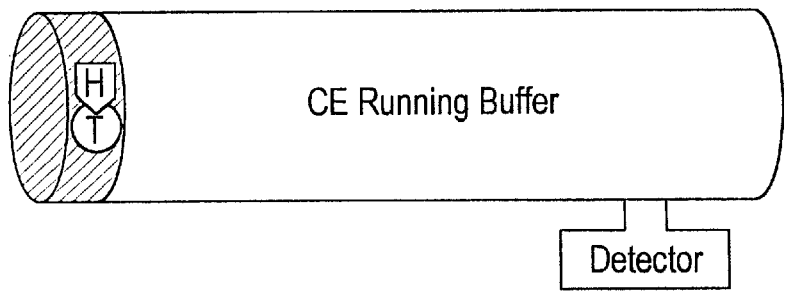

Step (5) : Inject running buffer plug into CE to push the target/sample plug closer to detector: [Optional for one CE run]

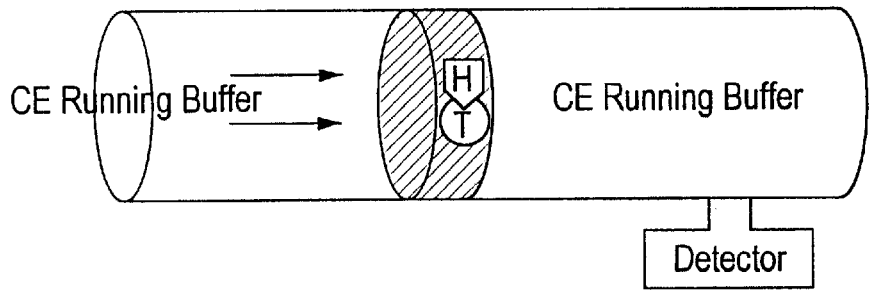

Step (6) : Start voltage and subject to CE
Step (7) : Monitor migration of target/hit complex and measure target/hit complex peak area
Step (8) : In separate runs, repeat steps (4) - (7) varying the duration of CE running buffer injections in step (5)
Step (9) : Measure decay of target/hit complex peak vs. its CE run time

*FIG. 1*

Single Detector, Multiple Injections

Step (1): Provide target 
Step (2): Provide sample possibly having hit compound
Step (3): Mix target and sample
Step (4): Inject target/sample (T/S) plug into CE having single detector
Step (5): [OPTIONAL] Inject running buffer (R/B) plug into CE to push the target/sample plug closer to detector.
Step (6): Repeat steps (4) and (5) as many times as desired <u>Examples:</u>

A) Repeat step (4) three times, no step (5):

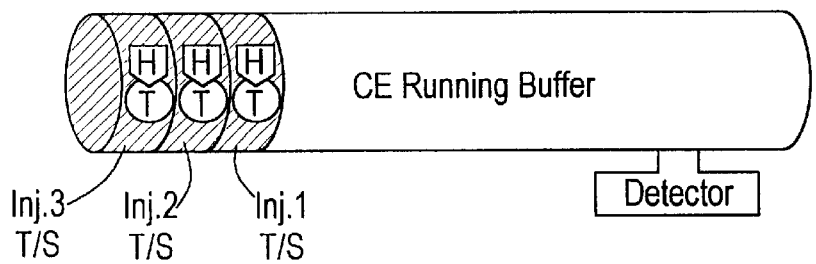

B) Repeat step (4) three times, step (5) once after the three T/S injections

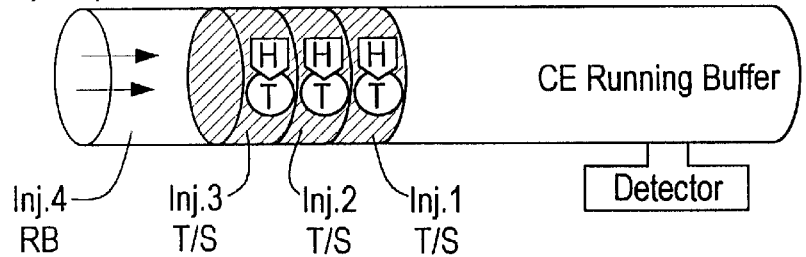

C) Alternate Step (4) and (5) three times:

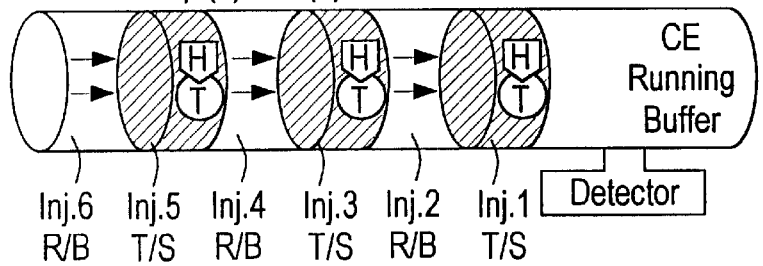

Step (7): Start voltage and subject to CE
Step (8): Monitor migration of target/hit complex and measure target/hit complex peak area
Step (9): Measure decay of target/hit complex peak

*FIG. 2*

Multiple Detectors

Step (1) : Provide target 
Step (2) : Provide sample possibly having hit compound 
Step (3) : Mix target and sample
Step (4) : Inject target/sample (T/S) plug into CE having multiple detectors

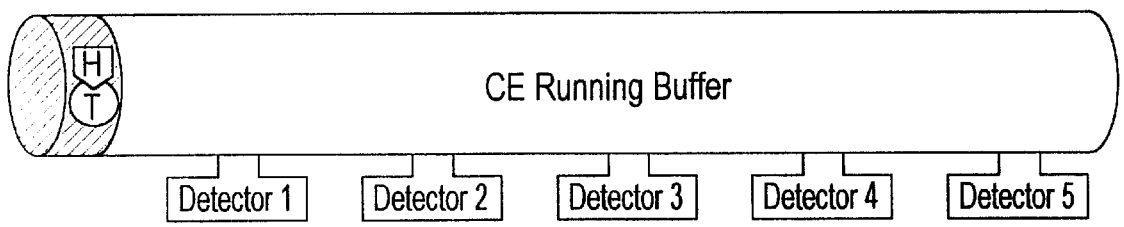

Step (5) [OPTIONAL] : As in Figure 2, Example B, inject a plug of CE
         running buffer to push the target sample plug closer to detector 1
Step (6) : Start voltage and subject to CE
Step (7) : Monitor migration of target/hit complex and measure
         target/hit complex peak area
Step (8) : Measure decay of target/hit complex peak vs. its CE run time

CAPILLARY ELECTROPHORETIC METHOD TO DETECT TARGET-BINDING LIGANDS AND TO DETERMINE THEIR RELATIVE AFFINITIES

This application claims the benefit of Provisional application Ser. No. 60/068,781, filed Dec. 24, 1997.

FIELD OF THE INVENTION

This invention relates generally to the discovery of new regulatory compounds, drugs, and/or diagnostic agents. In particular, it relates to capillary electrophoretic methods for detecting ligands binding to a known target molecule, and for determining the relative stabilities of ligand/target complexes, thereby allowing the ranking of different ligands according to their relative binding strengths to a common target. The invention encompasses methods of detecting moderate-to-strong binding ligands in mixtures that also have much higher concentrations of competing, weaker-binding ligands.

BACKGROUND OF THE INVENTION

Developing screens to identify new biologically active compounds can present unique and difficult challenges, especially when screening complex materials, particularly "complex biological materials": any material that may have an effect in a biological system. Examples include, but are not limited to: naturally occurring samples, products or extracts; various biological preparations; chemical mixtures; libraries of pure compounds; and combinatorial libraries. Examples of major screening problems include: detecting potential hit compounds that bind to a target of interest, especially ligands present at low concentrations in screened samples; accounting for unknown components that can interfere with screening agents; and determining the relative value of screened samples for further investigative efforts. As well, high concentrations of a weak or several weak, competing binder(s) can mask the signal from a moderate-to-strong hit compound occurring at a lower concentration in the same sample.

Recently, the use of capillary electrophoresis techniques has facilitated and improved the process of screening for unknown, biologically active compounds. For example, WO 97/22000 encompasses four broad embodiments of a capillary electrophoretic screening method, as follows.

(1) In a non-competitive embodiment of WO 97/22000, a target and complex biological sample are mixed together, then an aliquot of that target/sample mixture is subjected to capillary electrophoresis (CE), and the CE migration of the target is tracked. The target's migration pattern under these conditions are compared against a reference standard, typically the unbound target's migration pattern in the absence of any target-binding ligand.

(2) In a non-competitive, subtractive analysis embodiment of WO 97/22000, a target and sample are mixed together and then subjected to CE. The migration pattern of this mixture is compared to the migration pattern of a sample of the complex biological material alone. Any difference between the two migration patterns suggests the presence in the sample of a hit compound that can bind to the target.

(3) One competitive binding embodiment is provided in WO 97/22000, which tracks known, charged ligand: The target is first mixed with a complex biological material sample, and then with a known, charged ligand that binds tightly to the target, to form a sample/target/known ligand mixture. This method uses an essentially equilibrium setting when incubating target and known, tight-binding ligand together, so that the known, tight-binding ligand can displace any weaker-binding hit, prior to CE. This mixture is subjected to capillary electrophoresis and the migration of the known, charged ligand is tracked. (Thus, this method is useful when the target is not easily detected during CE.) Any difference in the known, charged ligand's migration pattern, when in the presence of both the target and a complex biological material sample, from the known ligand's migration pattern when in the presence of the target alone, indicates the presence of a candidate, unidentified target-binding ligand in that sample.

(4) In another competitive binding embodiment of WO 97/22000, the target's migration is tracked and the CE running buffer contains a known, weak-binding, competitive ligand. The target is mixed with a sample, and an aliquot of the mixture is subjected to CE in the presence of a known, relatively weak, target-binding 'competitor' ligand in the CE running buffer. The migration of the target is tracked during CE. The reference standard is the migration of a target plug alone in the known ligand-containing CE buffer, its migration being shifted by its weak, reversible binding to the known ligand dispersed in the CE buffer, as compared to the target's migration alone ligand-free buffer. This competitive screening method can detect a tight-binding hit compound in a target/natural sample mixture, because the hit binds up the target for the entire CE run and prevents the target's interaction with the known weak-binding ligand in the buffer. Therefore, the CE migration pattern of the target in the sample/target aliquot would shift back to the target's migration position as it would be in ligand-free running buffer. This method, too, is particularly useful when the unbound target is not easily detected in ligand-free buffer during CE.

While WO 97/22000 provides useful CE screening methods, they do not completely solve the screening problems listed previously.

Therefore, there remains a need for rapid and cost-effective screening tools for discovering new bioactive compounds and potential regulatory compounds that bind to essential molecules of key metabolic pathways. Also needed is a way of prioritizing candidate ligands and samples of material for further characterization. The present invention addresses these needs, by providing: a means of detecting unknown ligands that may be candidate, new, bioactive compounds; a means of ranking screened samples detected to contain candidate hit compounds or ligands, according to their relative binding strengths and value as potential sources of regulatory and diagnostic compounds; and a means of identifying effective and valuable, strong or moderate, target-binding ligands in the presence of weaker, competitive binders. Identifying and ranking those ligand-containing samples that form the most stable complexes with the selected target, saves time and resources spent on further isolation and characterization of hit compounds. The most stable ligands are potentially more effective and valuable as therapeutic, regulatory and/or diagnostic compounds and drugs.

SUMMARY OF THE INVENTION

The present invention provides: (1) a means to screen for target-binding ligands of a desired binding strength, in complex biological and other materials and mixtures; (2) a means to screen for the ligands or hit compounds of the desired affinity, even in the presence of weak-binding ligands in mixtures; and (3) a means to rank hit compounds according to their relative affinities. All aspects of the method can be performed on samples of pure hit compounds, partially purified hit compounds, and hit compounds present in complex biological mixtures.

The present invention provides simple and rapid, capillary electrophoretic methods for screening for and ranking ligands that do not require knowledge of a particular ligand's structure or concentration within the screened sample. In fact, it can be practiced on samples of complex materials, such as natural samples, that potentially contain one or more unidentified ligand(s) or hit compound(s) that bind to a selected target of interest. The migration of both the target and the target/hit compound complex must be detectable during capillary electrophoresis (CE). The hit compound should be detectable by its ability to alter the CE profile of the detectable target.

The present capillary electrophoretic screening methods allow one to detect hit compounds of any desired affinity or binding strength. Detection of weak, moderate and/or strong binding ligands is possible because the screened sample, once mixed and incubated with a select target, is injected into a CE capillary and electrophoresed. Electrophoretic conditions are optimized to detect hit compounds having a desired affinity for a selected target: e.g., ligands of any binding affinity (weak, moderate, or strong), only those with moderate-to-strong affinity, or only those with strong affinity for the target. The dissociation rate or stability of a particular hit compound/target complex during CE is related to the binding strength of that hit compound to a target. The complex's stability is also affected by such electrophoretic conditions as temperature, CE run time, and, buffer composition (e.g., its ionic strength, buffer ions, cofactors).

Therefore, using certain electrophoretic conditions, the hit compound/target complex can be stabilized so that any hit compound—whether weak-, moderate-, or strong-binding—is detected. Alternatively, the CE conditions can be chosen to destabilize the weak hit compound/target complex, so that weak ligands will dissociate much faster from a target than will strong ligands, during CE. The latter conditions will significantly or completely reduce a weak hit compound/target complex signal, but may only slightly reduce a strong hit compound/target complex signal. For example, a weak-binding hit compound/target complex is stabilized and detected when the temperature of the capillary is maintained relatively low, near the lower limit of viable CE temperatures (e.g., at about 5–10° C.), and the injected sample is subjected to a relatively short capillary electrophoresis (CE) run (e.g., within a range of about 0.5–5.0 minutes, preferably 1.0–2.5 minutes), prior to the detection point where the migration of any target and/or hit compound/target complex is tracked. If the CE is performed at a higher temperature, e.g., 25–45° C., a weak-binding ligand may dissociate and be undetectable, whereas a strong ligand may remain complexed.

One embodiment of the present screening method includes a known, charged, competitive, target-binding ligand in the capillary electrophoretic running buffer. This embodiment may be used if, when a sample is screened without a competitive ligand in the buffer, a hit compound does not detectably alter the mobility of the target upon complexation. When using a competitive ligand in the buffer, the target's CE peak is shifted upon its complexation with competitive ligand as the target migrates through the capillary, which serves as the reference CE profile. Binding of a hit compound to a target will prevent binding of the competitive ligand and thus, will change the migration pattern of the target from the reference situation.

In its ligand-ranking aspect, the method of the invention may be used to determine the relative stabilities of different ligand/target complexes during capillary electrophoresis. Specifically, the latter aspect of the present method allows one to rank various ligands or hit compounds that are found to bind to a common target of interest, according to their "relative stability"—i.e., their respective ability, relative to each other, to remain complexed to that target under the same CE conditions. Some parameters influencing the stability of a target/ligand complex in CE include: the ligand's on-rate and off-rate; capillary temperature; pH of the background buffer in the capillary; and ionic strength of the background buffer. Other factors affecting the stability of a target/ligand complex will be apparent to those of ordinary skill in the art of capillary electrophoresis.

One particularly useful application of this ligand-ranking method is in drug discovery. The method is useful for detecting candidate, unidentified ligands that bind to a selected target, in pure compound libraries or complex materials, such as biological samples or synthetic chemical mixtures. As well, unknown target-binding ligands detected to be present may be ranked in terms of their relative affinities or target-binding strengths during CE, early during drug screening and isolation protocols. Ranking of ligand-containing samples helps to save time and resources spent on follow-up isolation and characterization of potential new bioactive hit compounds.

Another particular useful application of this invention is the ability to detect strong binding ligands in the presence of higher concentrations of competitive weak binding ligands. The electrophoretic conditions affect the stability of weak and strong ligand/target complexes to different degrees. Therefore, one can set the CE conditions so that weak ligand/target complexes will dissociate completely during the CE run, but strong/ligand complexes will remain present at a level above the detection limits of the detector. The ability to identify only the samples that contain strong ligands, is very important as it helps to save time and resources spent on screening and isolation of potential, new, bioactive hit compounds.

BRIEF DESCRIPTION OF THE DRAWINGS

FIG. 1 depicts an embodiment of the method of the invention using a single detector in a capillary electrophoretic instrument and multiple CE runs;

FIG. 2 depicts an embodiment of the method using a single detector in a CE instrument and multiple injections of a sample/target mixture within a single CE run;

FIG. 3 depicts an embodiment of the method using multiple detectors in a CE instrument;

DETAILED DESCRIPTION

Figure 5:
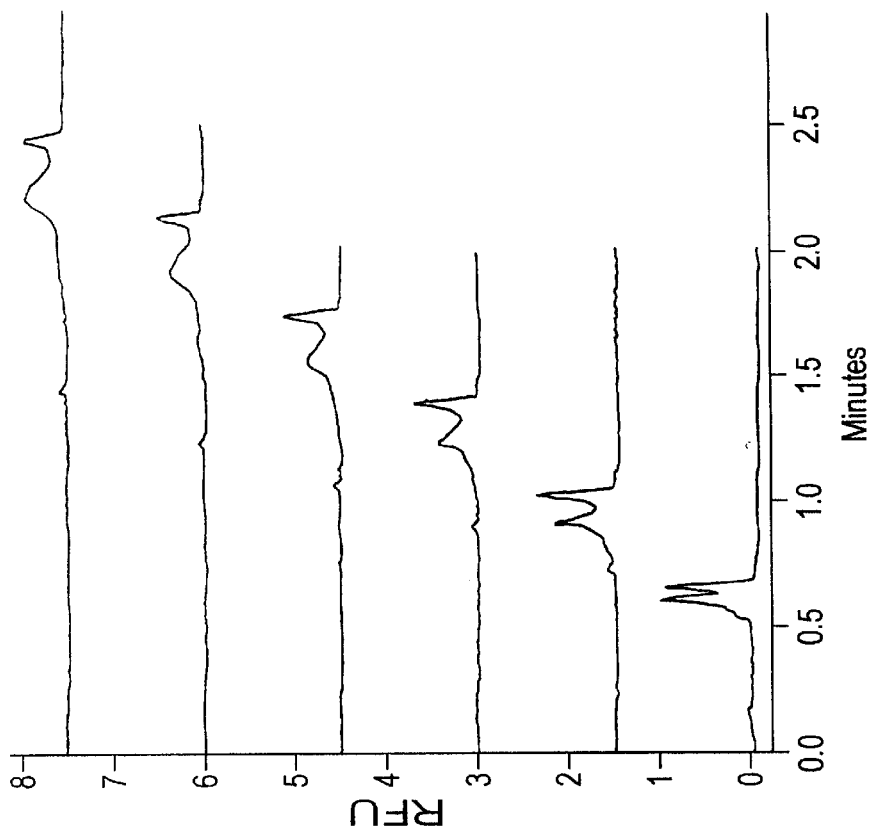
FIG. 5 depicts a series of CE runs, as in FIG. 4, but the sample contains both LTG and 16 pM of a strong binding hit compound, ethoxyzolamide (EZ)

The screening method of the invention uses capillary electrophoresis, performed at different temperatures, for different time intervals, and/or different buffer compositions, to detect in a sample of material for screening—particularly complex biological materials, that include natural samples or extracts, pure compounds, or chemical mixtures—ligands that bind to a selected target at a desired binding strength. The method can also be used to determine the relative binding affinities—weak, moderate, or strong—of various hit compounds which bind to the selected target. Depending on the particular application, these hit compounds can be known or unknown compounds, or ones previously unidentified as ligands of the selected target.

The present method observes the capillary electrophoretic (CE) profile of a selected target (TG) after its incubation with a sample possibly containing a ligand or "hit compound" (HT) that binds to the target. The method tracks the migration peak of the unbound target (TG) during CE, and that of the hit compound/bound target (HT/TG) complex, and determines the relative rate at which the HT/TG complex peak is reduced or disappears during the course of the CE run. This CE information allows one to rank various ligands or hit compounds, whether known or unknown, according to their relative affinities for a selected, common target (i.e., the relative stabilities of the different ligand/target complexes, relative to each other, in a given set of CE experiments comparing the relative dissociation rates of several hit compounds from the same target). The terms "affinity" and "relative affinities" are used in a general sense, and do not necessarily refer to a hit compound's "binding affinity" to a target in an equilibrium situation.

One embodiment of the present method uses a known, charged, weakly target-binding competitive ligand in the CE running buffer, and can detect hit compounds that compete for the same binding site of a target, and can rank the relative affinities of detected hit compounds.

The present method generally comprises: (1) providing a predetermined concentration of a selected, CE-detectable target; (2) providing a sample potentially containing one or more hit compound(s) to the target; and (3) mixing the selected target and sample and incubating the resulting target/sample mixture for a time sufficient to allow a target/hit compound complex, if any, to form; (4) injecting an aliquot of the target/sample mixture from step (2) into a CE instrument, for a pre-selected length of time; (5) subjecting the aliquot of target/sample mixture to capillary electrophoresis optimized to detect a hit compound at or above a selected binding strength; and (6) observing the CE profile of the injected target/sample aliquot at one or more detection point(s) in the CE instrument. Additionally, the CE profile of the target/sample aliquot from step (6) may be compared with a CE reference. Specifically, step (6) of the method tracks the migration of both the unbound target and any bound target/hit compound complex during capillary electrophoresis. Optionally, for some embodiments of the method, following injection of the target/sample aliquot (step 4) and before CE (step 5 of the above-described method), an aliquot of CE running buffer may be injected into the CE instrument behind the target/sample aliquot to push the target sample aliquot closer to the detector(s), which reduces its run time prior to detection.

The CE reference may be the migration of the unbound TG peak during one or more CE runs of the unbound target samples alone (absent any ligand), performed at the same CE conditions as the ones used to detect hit compounds. By using the resulting information regarding the relative stability of each target/hit compound complex during CE, one can determine and rank the hit compound's relative binding strength or affinity for a given target in comparison to other hit compounds.

When the method is used to detect a sample containing a hit compound, it may be followed by standard techniques of fractionation, purification, isolation, characterization, and the like, to isolate, to identify, and/or to characterize the ligand detected. This isolated compound is a candidate, unknown or previously unidentified ligand for the selected target used to perform the screening method, and may be a regulatory compound.

Single-Detector, Multiple-Run Method

One embodiment of the present method uses a single detector placed at a single detection window in the capillary, as shown in FIG. 1, and multiple CE runs. In this embodiment, steps (4)–(7) of the method are repeated a selected number of times. A selected target and a sample potentially containing a hit compound are mixed together in steps (1)–(3). In step (4), a target/sample plug or aliquot to is injected into the CE instrument. Optionally, in step (5) (i.e., which is optional for one of the CE runs), before the voltage is turned on, an aliquot of CE running buffer may be injected to further push the target/sample plug towards the single detection window in the CE capillary. In step (6) of FIG. 1, voltage is applied to the capillary and the target/sample aliquot is subjected to capillary electrophoresis. In step (7), the migration of the unbound target and the HT/TG complex is monitored at the detection window.

In step 8, one repeats steps (4)–(7) a desired number of times, but in each repeat, the injected target/sample aliquot undergoes a different CE run time. In each repeat of steps (4)–(7) of the process, particularly at step (5), one varies the length of time or duraion for which the running buffer aliquot is injected into the CE instrument, so as to push the target/sample plug to the desired CE starting point. A longer injection pushes the target/sample aliquot closer towards the CE detection window, thereby allowing a shorter CE run prior to detecting the migration peaks of the unbound target and/or the target/hit compound (HT/TG) complex. Thus, the greater the amount of the buffer aliquot injected, the closer it is to the detector.

In step (9), one compares the sequential series of CE profiles of the target/sample mixture generated in step (8) by repetitions of steps (4)–(7), with each other and with a CE reference (such as the CE profile(s) of the unbound target alone). These profiles, showing the CE profiles of the target/sample plug at different time intervals, allow one to determine whether a hit compound/target complex has formed, and the rate at which that target-binding hit compound dissociates from the target. Specifically, by measuring and comparing the amount of target/hit compound complex present in each different CE run (i e., measuring the area of the complex's CE peak versus its CE run time), one can determine how quickly, the complex dissociates. These collective CE profiles thus give information about the relative stability of that particular hit compound/target (HT/TG) complex, and thus, about that hit compound's relative affinity for the target. This information can be collected for a variety of hit compounds and used to rank their relative target affinities.

Single-Detector, Multiple-Injection Method

As shown in FIG. 2, another embodiment of the method performs a single capillary electrophoretic run, using a single detector and multiple injections of the target/sample aliquot that are spaced apart along the axis of the capillary. Step (4), and optionally, step (5), of the general method of the invention (injection of an aliquot) is/are repeated several times. In this multiple-injection embodiment of the method, one can optionally inject an aliquot of CE running buffer after each injection of a target/sample aliquot or plug—that is, buffer can be introduced between individual injections of the target/sample plugs. After injection of the last plug, voltage is applied and all target/sample plugs are subjected to capillary electrophoresis, according to step (7) of the method. Subsequently, as in step (6) of the general method, the migration of the unbound target and HT/TG complex in each injected plug is observed as each plug travels past the single detector. The series of CE profiles of the target/sample plugs, originating from the multiple target/sample injections, can be compared with each other and with a CE reference (e.g., the CE profiles of a sample of unbound target alone). Analysis of the data can then be performed, as with the single-detector method.

Multiple-Detector Method

Alternatively, as shown in FIG. 3, another embodiment of the method uses multiple detectors in the CE instrument, and requires only a single capillary electrophoretic run (although several CE runs could be performed as desired). These detectors detect the migration peaks of the unbound target and any HT/TG complex at multiple detection windows along the axis of the capillary, as the target/sample aliquot or plug migrates along the capillary from the inlet towards the outlet during CE. FIG. 3 shows the general method of the invention, as described previously. In step (4), a target/sample plug (i.e., aliquot of the target/sample mixture) is injected into the capillary of a CE instrument. In this multiple-detector embodiment of the method, injecting an aliquot of CE running buffer after injection of the sample plug is optional (step (5) in FIG. 3). Voltage is applied and the sample plug is subjected to capillary electrophoresis, according to step (6) of the method. Subsequently, the migration of the unbound target and any HT/TG complex in the injected plug is observed as it migrates past each of several sequential detection windows along the CE capillary (Detector 1–Detector 5 in FIG. 3). At each subsequent detector, more time has passed so that any HT/TG complex has spent more time in the capillary and will have had more time in which to dissociate. By observing the CE profile generated at each detector, one determines, as in the single-detector embodiment, whether the sample contains at least one hit compound and how quickly the target/hit compound complex dissociates. The series of CE profiles of the target/sample plug generated from the multiple detection points can be compared with each other and with a CE reference (e.g., the CE profile(s) of a sample of unbound target alone).

In a multiple-run variant of this method, one can maximize the information generated by performing multiple CE runs, each of a different duration (as in the single-detector, multiple-run method), on a multiple-detector CE instrument. One thus increases the number of CE profiles generated (the total being the number of detectors multiplied by the number of runs performed).

Competitive-Binding Method

As well, the method of the invention has a competitive-binding embodiment, which can be used to detect a potentially unknown hit compound or to rank the relative affinities of several ligands to a target. This embodiment is particularly useful in situations where a hit compound may bind to the target but does not shift the target's CE migration detectably. This variation includes in the CE running buffer, a predetermined concentration of a known, weak-binding, preferably charged, competitive ligand (CL) to the selected target (TG). When bound to the target, the competitive ligand must shift the CE mobility of the target detectably. The known, weak-binding competitive ligand could be, for example, a natural compound, a synthetic compound, an antibody, or a drug known to bind to the target of interest.

For this competitive-binding embodiment of the method, the CE reference may be the target's migration peak as shifted by the target's rapid association and dissociation from the known competitive ligand. This competitive-binding CE method may be used with all three formats described in FIGS. 1–3 (single-detector plus multiple CE runs, single-detector plus multiple injections, and multiple-detector).

The method of the invention may also be used to determine the relative affinities of several ligands or hit compounds found to bind to a selected target.

The following, non-limiting, exemplary protocols illustrate some applications of the method of the invention: either using no competitive ligand in the CE running buffer (Ligand-ranking Method A) and different CE run times; using the competitive-binding variation (Ligand-ranking Method B) and different CE run times; using different temperatures (Ligand-ranking Method C); or different buffer compositions (Ligand-Ranking Method D).

Ligand-Ranking Method A

An embodiment of the ligand-ranking method that can detect hits generally comprises the following steps. A predetermined concentration of a selected target (TG) is mixed with a sample determined to contain a hit compound (HT), to form a target/sample mixture. The HT may be pure, partially purified, or unpurified (e.g., the HT may be present in a sample of complex biological material). The target/sample mixture should be incubated for enough time to allow formation of a complex of the hit compound and the target (hereinafter "the HT/TG complex"): e.g., 0.5–30 minutes, preferably 1–5 minutes.

An aliquot of the target/sample mixture is injected into an open-tube capillary in a CE instrument. Optionally, this target/sample injection is followed by an pressure injection of CE running buffer. (The injection step is optional for usually the first or last CE run, as one may wish that injected aliquot to run the full length of the capillary from the injection point to the detector.) In the single CE-detector embodiment of the method, the running buffer is injected for different lengths of time over a series of CE runs, to push the injected target/sample aliquot to different CE starting points, relative to the detector. After injection of the target/sample aliquot and the CE running buffer, voltage is then applied to subject the target/sample plug to CE. One can observe the migration profile of the target/sample aliquot after different capillary electrophoresis run times and thus determine the rate of HT/TG complex dissociation over different CE times.

The migration of both the HT/TG complex and the unbound TG is monitored at the detection window during the CE step. The HT/TG complex and the unbound TG must have different electrophoretic migration times so that they will separate from each other. The peak areas of the HT/TG complex and the unbound TG are determined during CE. Those peak areas are used to determine the percentage of total target complexed with the hit compound (% HT/TG complex), according to the following formula (I):

$$\% \ HT/TG \ complex = \frac{[HG/TG \ complex \ peak \ area]}{[HT/TG \ complex \ peak \ area] + [unbound \ TG \ peak \ area]} \times 100\%$$

The rate at which the percentage of HT/TG complex decreases in relationship to the complex's CE migration time, correlates to the affinity of the HT (i.e., the relative stability of the HT/TG complex). The rate at which % HT/TG complex decreases, may be determined by observing the migration profiles of the target at different CE run times. One can achieve different run times by: using different injection times of the CE running buffer in a series of CE runs on a single-detector CE instrument; sequentially injecting multiple target/sample plugs into a single-detector CE instrument and subjecting them all to CE at one time, or by observing the migration profiles of the target/sample plug as it migrates past multiple detection windows in a capillary in a multiple-detector CE instrument. This experiment can be performed at different capillary temperatures. In general, lower capillary temperatures help to test the relative affinities of weaker binding ligands, because HT/TG complexes are more stable at lower temperatures. One can thus compare the percentage of HT/TG complex against CE temperature—the more stable complexes will give a higher percentage of HT/TG complex for a given CE run time, at higher temperatures.

Ligand-Ranking Method B Using Known Competitive Ligand

Another embodiment of the present Ligand-ranking method uses a known competitive ligand to a selected target, preferably a weak-binding one. The competitive-binding method generally comprises the following steps.

One mixes a predetermined concentration of the target (TG) with a sample determined to contain a hit compound (HT), to form a target/sample mixture. The HT may be pure, partially purified, or unpurified (e. g., the HT may be present in a sample of complex biological material). The target/sample mixture should be incubated for enough time, e.g., at least 1 minute, to allow the HT/TG complex to form. An aliquot or plug of the target/sample mixture is injected into an open-tube capillary (CE).

A weak-binding, charged competitive ligand (CL) is added to the CE running buffer (RB) to shift the migration of any TG that is not bound to the hit compound, by forming a rapidly associating and dissociating complex of the competitive ligand and target (hereinafter "CL/TG complex") during CE migration. Optionally, injection of the target/sample aliquot is followed by an injection of the CE running buffer. In a single CE-detector, multiple-CE run embodiment of the method, the running buffer is injected for different lengths of time over a series of CE runs, to push the injected target/sample aliquot to different starting points, relative to the detector. This method allows one to observe the migration profile of the target/sample aliquot after different durations of capillary electrophoresis, and thus, to determine the rate of HT/TG complex dissociation over different times. After injection of the target/sample aliquot and the CE running buffer, voltage is then applied to subject the target/sample plug to CE. The migration of the HT/TG complex peaks and the TG peak, as shifted by the TG's interaction with the CL, is monitored. The areas of the HT/TG complex peak and the CL-shifted, unbound TG migration peak are determined at different time intervals after voltage has been applied. Those peak areas are used to determine the percentage of total target existing in the HT/TG complex form (% HT/TG complex), according to the following formula (II):

$$\% \ HT/TG \ complex = \frac{[HG/TG \ complex \ peak \ area]}{[HT/TG \ complex \ peak \ area] + [CL\text{-}shifted \ TG \ peak \ area]} \times 100\%$$

The rate at which the % HT/TG complex decreases in relationship to the complex's CE migration time, correlates to to the relative affinity of the hit compound (i.e., the relative instability or stability of the HT/TG complex). This rate of % HT/TG complex decrease is determined by observing the migration peaks after different CE run times.

A variation of the method of the invention may make use of multiple detectors placed at different positions along the CE capillary length. The migration of any unbound target and of any HT/TG complex is monitored at each detector as the analytes travel past each detector. When this embodiment is used to rank the relative affinities or binding strengths of different ligands or hit compounds that bind to a common target, the affinities are calculated according to the amount of hit compound remaining complexed to the target.

Ligand-Ranking Method C Using Temperature Variation

Another embodiment of the present ligand-ranking method varies the temperature at which CE is performed, preferably within a range of about 4–45° C. It generally comprises the following steps.

After injection of the target/sample aliquot, voltage is then applied to subject the target/sample plug to CE. The CE capillary temperature is held at the lower limit, e.g., about 5° C. The migration of HT/TG complex and the unbound TG is monitored. The peak areas of the HT/TG complex and the unbound TG are determined and used to calculate the percentage of total target complexed with the hit compound (% HT/TG complex, calculated according to formula I in Ligand-Ranking Method A)).

Then the experiment is repeated, at increasingly higher CE temperatures. One observes the decrease in percentage of HT/TG complex over time, as CE temperature is increased, and determines the relative stability of that HT/TG complex. These temperature variation experiments can be performed on a variety of hit compounds. Strong ligand/target complexes will be more stable at higher temperatures and, thus, will dissociate to a lesser degree than weak ligand/target complexes. This temperature variation of the method of the invention can be performed using different CE run times and a single detector, or multiple detectors placed at different positions along the CE capillary length.

Ligand-Ranking Method D Using Different Buffer Compositions

Another embodiment of the present ligand-ranking method generally comprises the same steps as in Ligand-Ranking Method C. However, instead, of temperature changes, the salt concentration (i.e., ionic strength) of the CE running buffer is varied, within, e.g., the 10–100 mM range. Higher salt concentrations tend to help to stabilize target/hit compound complexes. Therefore, lower salt concentrations favor detection of tighter or stronger binding hit compounds.

Process for Finding Strong-binding Hits in Complex Biological Material Using the Ligand-ranking Method The method of the invention can be used to detect, identify and characterize, both easily and rapidly, strong-binding ligands or hit compounds present in samples of complex biological materials (e.g., natural extracts or synthetic compound mixtures). This method is successful even if the sample contains high concentrations of weak-binding, competitive hit compounds, which can often mask low concentrations of strong-binding hit compounds to a selected target of interest.

Before the screening process, all CE conditions have to be optimized to detect hits with the desired range of affinities for the selected target, as will be appreciated by one of ordinary skill in capillary electrophoresis. One must define criteria for determining what are a weak-binding hit compound (WB) and a strong-binding hit compound (SB) in the present method to determine relative stability of a hit compound/target complex. For instance, a weak binder (WB) may be a ligand forming a complex with the target (TG) whose CE migration peak area is reduced by over 90% after approximately 1 minute into the CE run, especially by 1.5–5.0 minutes. A strong binder (SB) may be a ligand forming a complex with the TG whose CE migration peak area becomes no more than 50% reduced after approximately 1.5–5.0 minutes (e.g., 2.5 minutes) into the CE run. The cutoff for determining the relative binding strength of different ligands or hit compounds is determined primarily by a combination of factors, including but not limited to: capillary length; the distance between the CE starting point and the detector; CE run time; voltage and temperature during CE; and buffer composition, such as its pH and/or salt concentration (e.g., NaCl). For example, strong binders (SB) can be found by using higher temperatures (e.g., about 25–45° C.), a longer CE run time (e.g., within a range of about 2.5–10.0 minutes), and/or longer capillaries (e.g., about 10–100 cm). Weaker binders (WB) can be found using lower temperatures (e.g., about 5–25° C.), shorter CE run times (e.g., about 1.0–3.0 minutes), and/or shorter capillaries (e.g., about 0.5–10 cm). In general, buffer pH values may be about 3–10, CE voltages may be about 5–30 kV, and salt concentrations may be within the range of about 0–100 nM.

The method of the invention is particularly advantageous in identifying, in a screened sample, candidate hit compound (s) having a binding strength higher than a selected threshold, and for determining their relative binding strength. "Moderate-to-strong binding" ligands and "weak-binding" ligands have faster off-rates ($k_{off}$) and higher dissociaton constants ($K_D$), and form target/ligand complexes that hold together for little or none of a capillary electrophoretic run, i.e., target/ligand complexes that are unstable and fall apart quickly before reaching detector. In contrast, "strong-binding" or "tight-binding" ligands have lower dissociation constants and slow off-rates, forming target/ligand complexes that generally remain bound as they migrate past a detector during capillary electrophoresis. Typically, but not always, ligands of a particular binding strength have the respective characteristics shown in Table 1.

TABLE 1

| Ligand | Approx. $K_D$ range | Approx. $K_{off}$ range | Functional Definition |
|---|---|---|---|
| Strong-binding | <10 nM | <0.01 ($s^{-1}$) | Target/Ligand complex holds together such that its migration peak is reduced no more than 50% afer about |

TABLE 1-continued

| Ligand | Approx. $K_D$ range | Approx. $K_{off}$ range | Functional Definition |
|---|---|---|---|
| | | | 1.5–5.0 minutes into a CE run |
| Moderate-to-strong-binding | 10 nM–10 μM | 0.01–1.0 ($s^{-1}$) | Target/Ligand complex dissociates such that its migration peak is reduced by about 51–90% after about 1.5–5.0 minutes into a CE run |
| Weak-binding | >10 μM | >1.0 ($s^{-1}$) | Target/Ligand complex dissociates such that its migration peak is reduced by about 91–99% after about 1.5–5.0 minutes into a CE run |

Once the CE conditions are chosen, the screening itself uses the fact that the rate of ligand/target complex dissociation is different for weak ligand/target and strong ligand/target complexes. Therefore, using optimized CE conditions, one can achieve complete dissociation of weak ligand/target complexes (or at least enough dissociation so that any remaining such complex falls below the detection threshold). On the other hand, the strong ligand/target complex dissociates to some degree, but some complex remains at a concentration above the detection limits of the detector. Thus, the CE detector will detect only the signal from the strong ligand.

This method allows one to determine whether one or more strong ligand(s) is/are present in the biological sample even in the presence of high concentration of weak ligands. This fact will hold true as long as the strong ligand/target complex is formed in the pre-capillary incubation step of biological sample with a target in a concentration above the detection limits of the CE detector.

One may use capillary electrophoresis or any other screening method to determine whether a sample of complex material potentially contains unidentified ligand(s) or hit compound(s) that can bind to a target of interest. The method of this invention can advantageously guide bioactivity-guided fractionation of complex material being screened for hit compounds.

In order to use the method to help purify the strong-binding (SB) hit, one should run general separation or fractionation techniques on the screened material and collect resulting fractions. Non-limiting examples of separation techniques include liquid/liquid extraction, solid-phase extraction, and high-performance liquid chromatography (HPLC) fractionation.

Each fraction of the fractionated sample should be tested according to the present capillary electrophoretic ligand-ranking method. Fractions with no SB signal and a low or no WB signal can be discarded. One should keep fractions that have a positive SB signal, or that have no SB signal but do have a high WB signal. (A very high WB signal may mask an SB.)

SB-positive fractions may be further fractionated by standard methods until the candidate strong binder is isolated. That is, one focuses on isolating the specific SB from the SB-positive fractions, performing further fractionation and ligand-ranking testing of the SB-positive fractions as needed until the SB is isolated.

SB-negative fractions having a high WB signal may be subjected to one or more rounds of additional separation and ligand-ranking steps as described above. That is, SB-negative fractions may be subjected to further separation or fractionation. The resulting new fractions are subjected to further testing according to the ligand-ranking method of the invention. Again, one discards those new fractions having no SB and a low or no WB signal. New fractions exhibiting a strong SB signal are kept and subjected to standard techniques for isolating the candidate SB compound. The result is that one only investigates fractions having a strong binding signal in the capillary electrophoretic ligand-ranking method of the invention.

Once a fraction of complex biological material has been determined to contain a hit compound of interest, the compound can be isolated from that fraction and examined to determine whether it has or has not been previously identified as a ligand that can bind to or interact with the target. The isolated compound can be tested for therapeutic efficacy or pharmokinetic properties against the target.

EXAMPLES

FIGS. 4–10 illustrate results from examples of the method of the invention. In all cases, the target-containing sample ("LTG sample") contained 16 nM fluorescein-labelled human carbonic anhydrase II, HCA-II, as the labelled target (LTG), and 10 mg/mL bovine serum albumin (BSA) in 100 mM TAPS/Tris buffer at pH 7.4. Some samples were incubated with a hit compound that can bind to HCA-II, while others were not. Each sample was pressure-injected for 10 seconds into a polyvinylalcohol-coated capillary with a 50-$\mu$ inner diameter, in a Beckman PACE 5000 capillary electrophoresis (CE) instrument. The sample injection was followed by an optional, low-pressure (0.5 psi) injection of CE running buffer, comprising 50 mM CAPSO/Tris buffer at pH 9.2, and a known competitive ligand (C), 10 $\mu$M carzenide. The CE running buffer was injected into the CE instrument for different lengths of time after the injection of the LTG sample, to push the LTG sample to varied distances from the detection window during CE. (This running buffer injection is optional.) For FIGS. 4–7, the running buffer (RB) injection times were respectively, from the lowest plot to the uppermost plot: 2.4 minutes, 2.2 minutes, 1.7 minutes, 1.1 minutes, 0.6 minute, and 0 minute. After injection of the CE running buffer, a voltage of 30 kV was then applied to the capillary and the migration of the fluorescently labelled target (LTG) was monitored at the detection window, at 6.8 cm from the injection end of the capillary. The laser excitation wavelength was 488 nanometers and fluorescence emission was monitored at 523 nanometers. The longer the low-pressure injection of the aliquot of CE running buffer, the less time it takes to visualize the LTG peak during a CE run, because it has less distance to migrate before reaching the detection window. All experiments were performed at 15° C.

Figure 4:
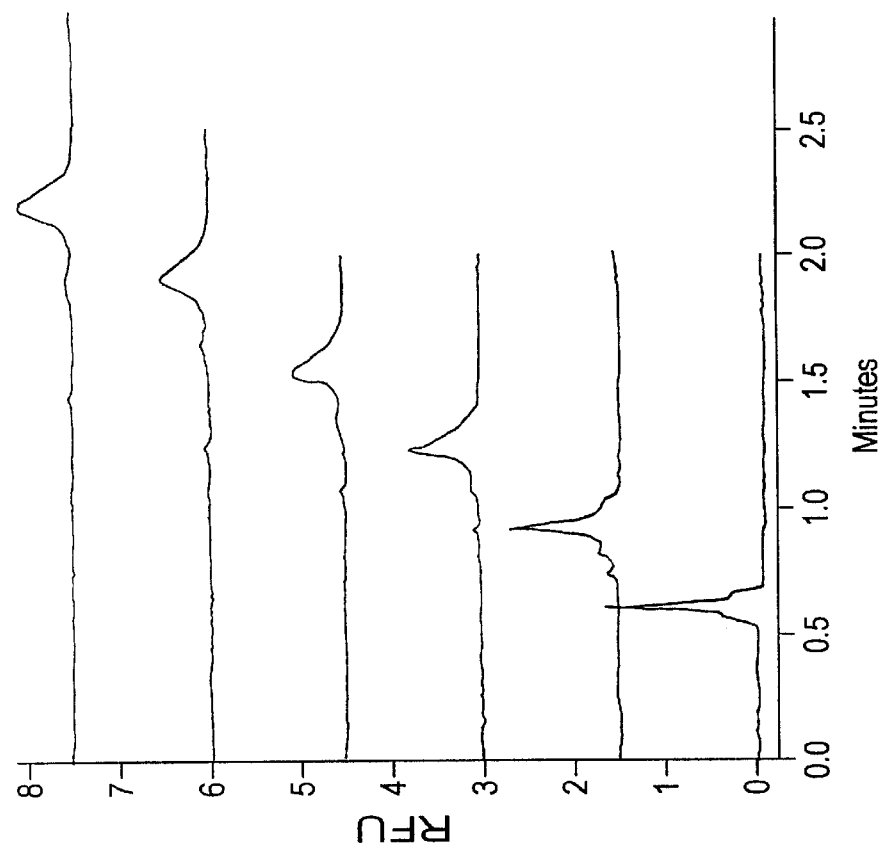
FIG. 4 depicts a series of capillary electrophoretic (CE) runs of different durations, where a sample of a labelled target (LTG)—fluorescein-labelled human carbonic anhydrase II—is injected without any LTG-binding hit compound, into a capillary with running buffer containing a weak-binding, charged competitive ligand.

FIG. 4 depicts a series of control capillary electrophoretic (CE) runs of a sample of fluorescein-labelled HCA-II as the labelled target (LTG), alone, without any LTG-binding hit compound. The CE running buffer has been injected at different times after the LTG sample was injected into the CE instrument.

FIG. 5 depicts a series of CE runs of a sample containing 16 nM LTG and 1 nM of the strong binding hit (SB), ethoxyzolamide (EZ), again with the running buffer being injected at different time intervals after sample injection.

The EZ/LTG complex peak is visible in all CE runs. This indicated that the EZ/LTG complex was stable for at least 2.4 minutes during the CE run.

Figure 6:
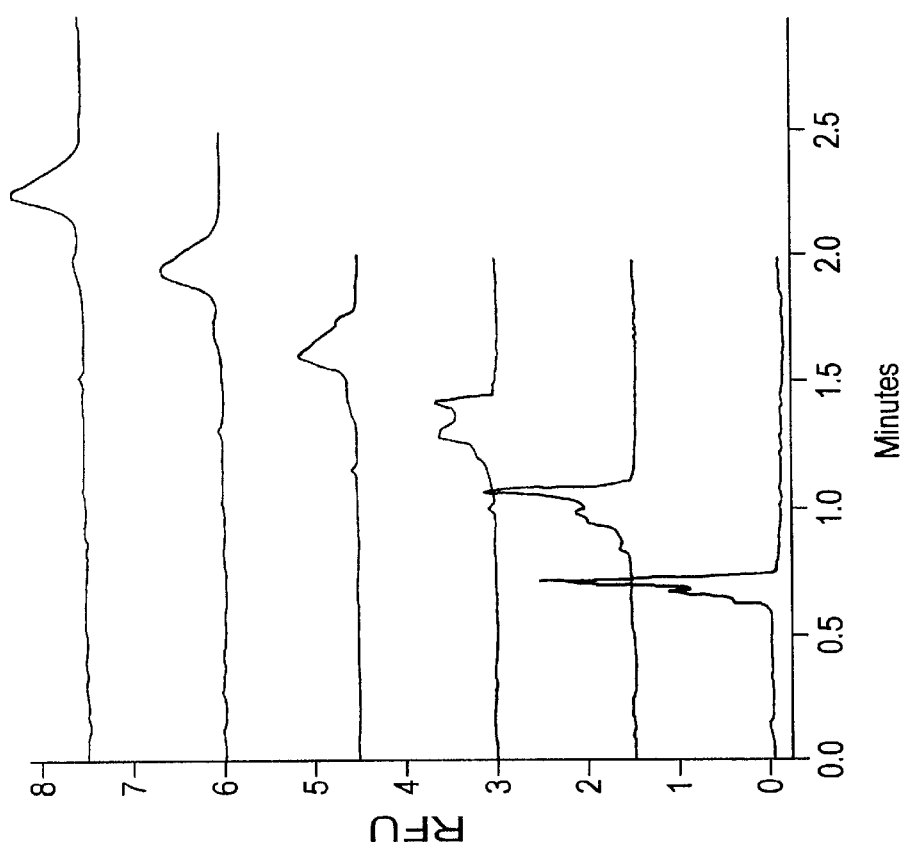
FIG. 6 depicts a series of CE runs of a sample containing 16 nM LTG and 9 $\mu$M of a moderate-binding hit compound, acetazolamide (AZ)

FIG. 6 depicts a series of CE runs of a sample containing 16 nM LTG and 9 $\mu$M of a moderate-binding hit compound to the LTG, acetazolamide (AZ). The AZ/LTG complex peak is visible only in the bottom four plots, indicating that the AZ/LTG complex had completely dissociated after migrating for 2.0 minutes during the CE run.

Figure 7:
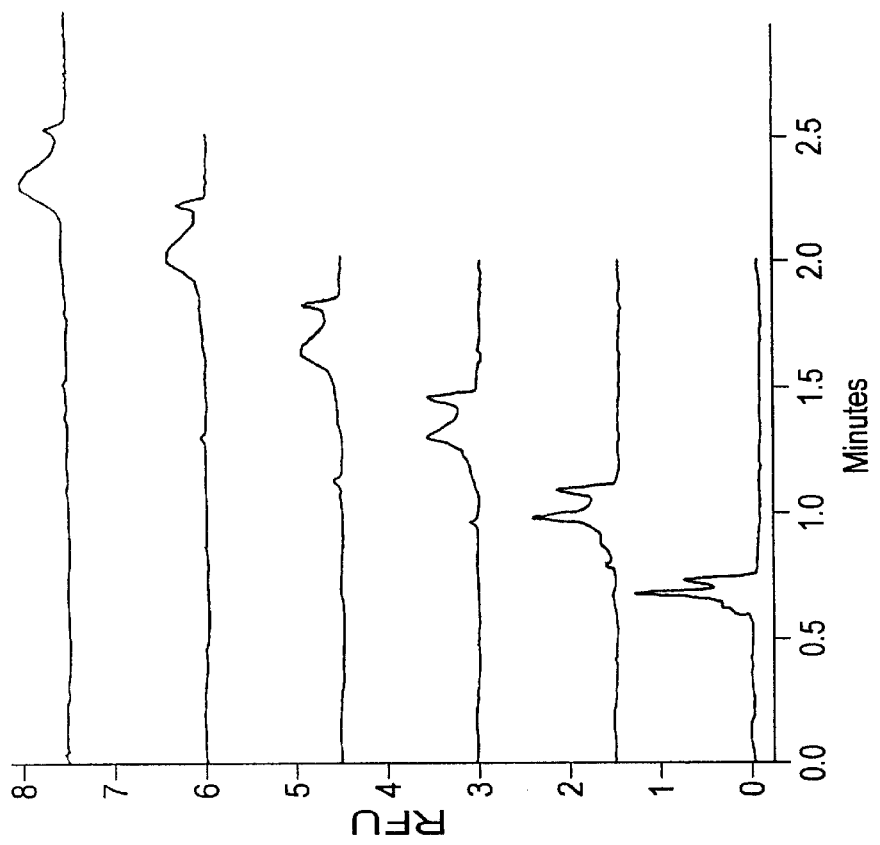
FIG. 7 depicts a series of CE runs of a sample containing 16 nM LTG incubated with a natural sample including an unknown, tight-binding hit compound.

FIG. 7 shows a series of CE runs of sample containing 16 nM LTG incubated with a natural sample including an unknown hit compound (HT). The HT/LTG complex peak is visible in all CE runs, suggesting that the hit is a strong binding ligand.

Figure 8:
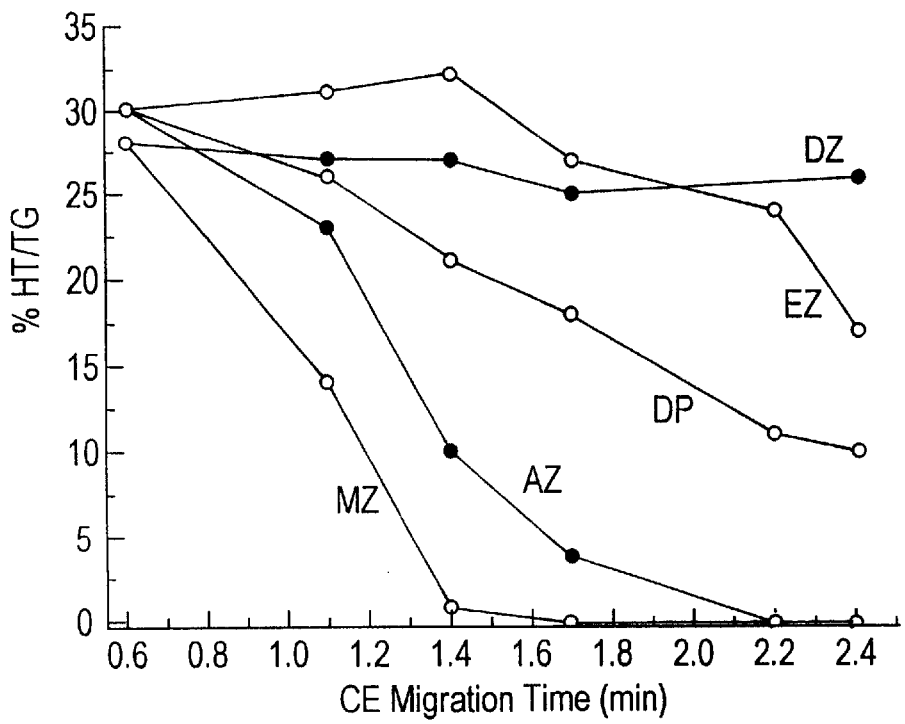
FIG. 8 depicts the relative stability plots for five different known hit compounds to the LTG, human carbonic anhydrase II.

FIG. 8 depicts the relative stability plots for five different known hits to the LTG. The hit compound concentrations were as follows: DZ=250 pM dorzolamide; EZ=1 nM ethoxyzolamide; DP=1 nM dichlorphenamide; AZ=9 nM acetazolamide; MZ=100 nM methazolamide. Based on these results, DZ is seen to be the most stable, while MZ is seen to be the least stable of the HCA-II binding hit compounds or ligands tested. This is consistent with the known relative binding strengths of the compounds.

Figure 9:
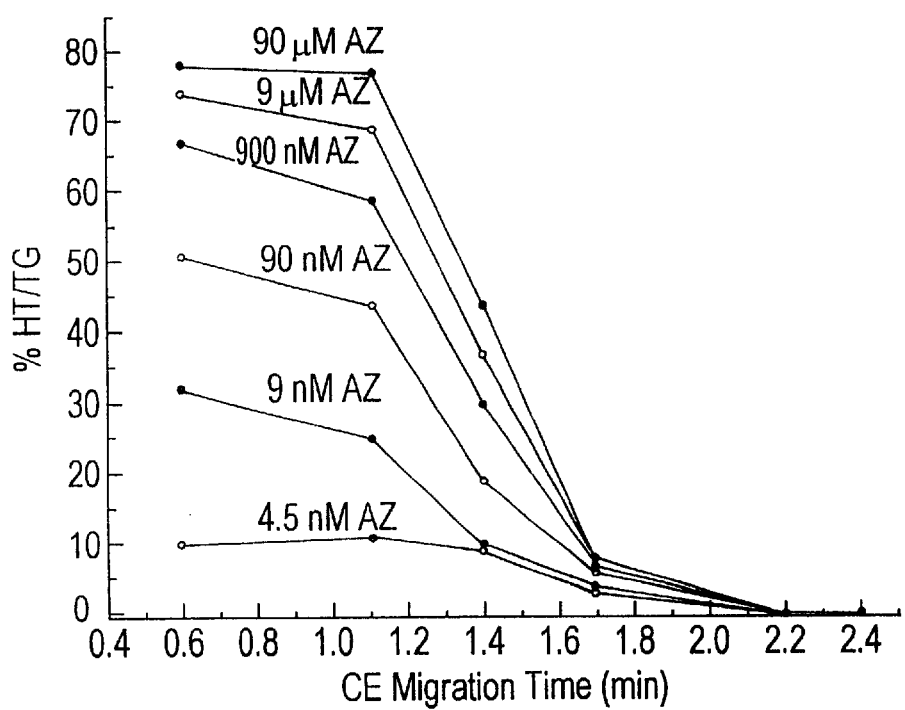
FIG. 9 depicts the relative stability plots for different concentrations of the hit compound, acetazolamide (AZ)

FIG. 9 depicts the relative stability plots for different concentrations of acetazolamide (AZ) as the hit compound. In all cases, the AZ/LTG complex had dissociated by the 2.2 minute CE run time. This indicated that the ability to measure the relative stability of the AZ/LTG complex was independent of AZ concentration and that the method of the invention yields meaningful results even when the hit compound concentration is unknown.

Figure 10:
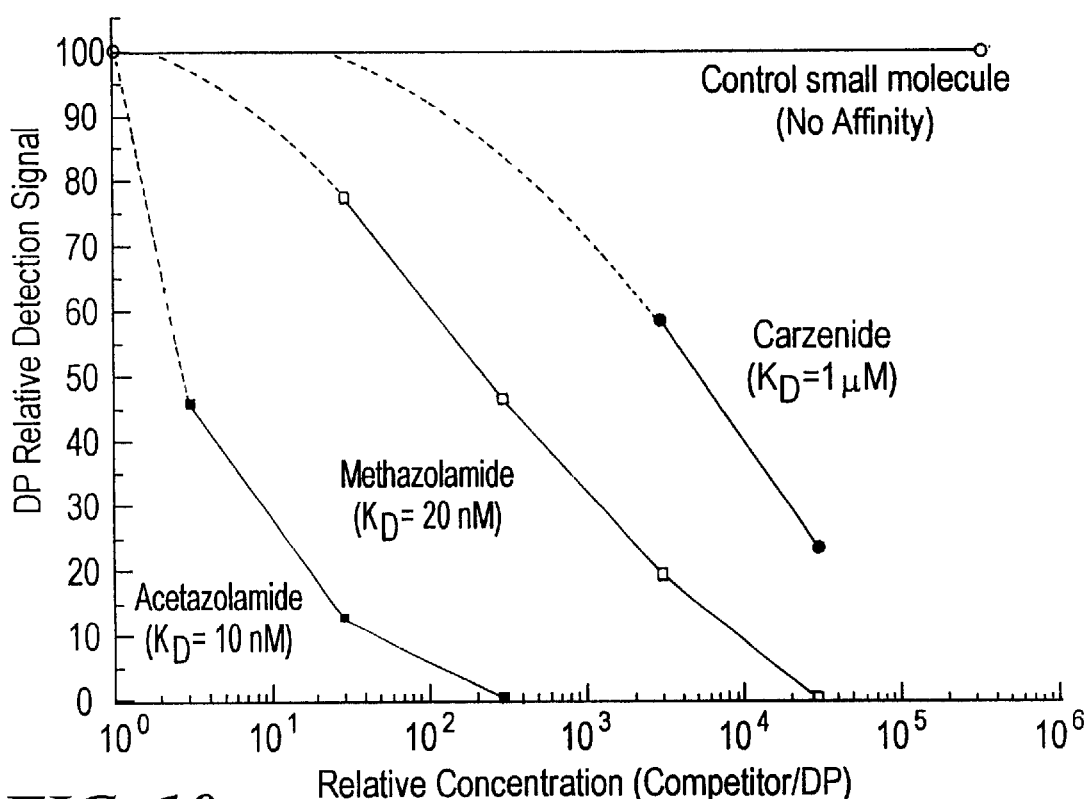
FIG. 10 depicts the relative CE signal of a tightbinding hit compound, dichlorophenamide (DP), in the presence of other ligands that also bind to the same target.

FIG. 10 depicts the relative signal of a tight-binding hit compound, dichlorophenamide (DP), in the presence of weaker, competitive ligands, under the same conditions as for the preceding figures. These results demonstrate the ability of the method of the invention to detect a tight-binding hit compound even in the presence of high concentrations of weaker, competitive binding compounds. In this experiment, the CE conditions were adjusted to detect only strong-binding compounds, i.e., those having a $K_D$ of about 2 nM or tighter. A constant concentration of DP was mixed with 16 nM of the target and with different competitive, target-binding ligands at different concentrations. The mixtures were subjected to CE and the signal from the DP/target complex was measured. (The other competitive compounds—carzenide, methazolamide, and acetazolamide—were too weak themselves to form stable complexes with the target.) In all cases, DP was detectable even when very high concentrations of a competitive ligand was present. For example, when carzenide was present at a 30,000-fold higher concentration than that of DP, the DP signal was over 20. In another example, MZ was present at a 3,000-fold higher concentration than that of DP, the DP signal was over 15.

Figure 11:
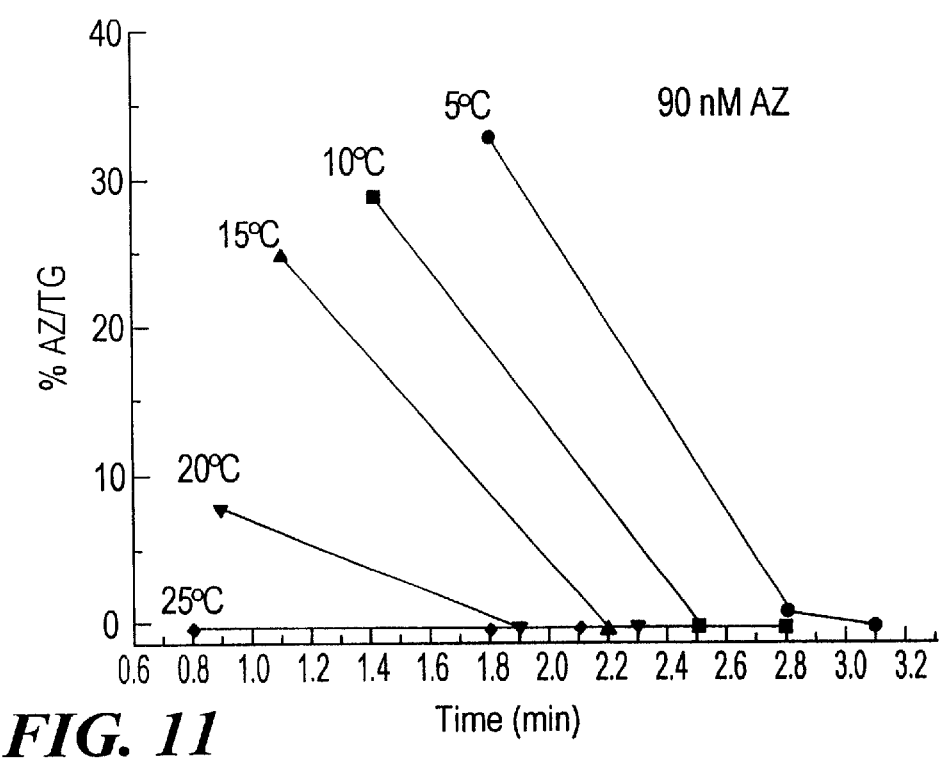
FIG. 11 depicts the relative stability plots of 90 nM of AZ at different capillary temperatures.

FIG. 11 indicates that lower temperatures can greatly enhance the sensitivity of the method of the invention, in detecting moderate-binding hit compounds like AZ. For example, AZ was undetectable at 1.8 minutes at 25° C., but easily detectable at 1.8 minutes at 5° C.

While the present invention has been described in conjunction with preferred embodiments, one of ordinary skill in the art, after reading the foregoing specification, will be able to effect various changes, substitutions of equivalents, and other modifications to the methods and compositions set forth herein.

What is claimed is:

1. A method to detect, in a sample of complex biological material, any candidate hit compound that binds to a selected target at or above a selected binding strength and to determine a stability, during capillary electrophoresis, of any target/hit compound complex detected, wherein the stability is determined to identify a relative affinity of a hit compound, said method comprising, in the order given, the steps of:

(1) providing a predetermined concentration of a selected target;

(2) providing a sample of complex biological material;

(3) mixing the target with the sample to form a target/sample mixture and incubating the target/sample mixture;

(4) injecting an aliquot of the target/sample mixture into a capillary electrophoresis instrument comprising a capillary having a single detection point;

(5) subjecting the target/sample aliquot to capillary electrophoresis under a set of conditions to detect any hit compound in the sample that binds to the target at or above a selected binding strength;

(6) tracking a capillary electrophoretic migration of the target in the injected target/sample aliquot at the detection point in the capillary electrophoresis instrument;

(7) repeating steps (4)–(6) one or more times, wherein each performance of steps (5)–(6) uses a different set of conditions for a different selected binding strength, wherein each injected target/sample aliquot undergoes a different capillary electrophoresis run time from other injected target/sample aliquot(s), thereby generating multiple capillary electrophoretic profiles, of the same target/sample aliquot, wherein the different conditions are optimized so that any complex, between the target and any candidate hit compound at or above each selected binding strength, generates a different result in tracking the capillary electrophoretic migration as in step (6);

(8) determining whether at least one capillary electrophoretic profile of the target generated from step (6), when compared to a reference standard, indicates a presence of any hit compound(s) binding to the target; and (9) determining the stability, during capillary electrophoresis, of any target/hit compound complex(es) detected, by comparing the multiple capillary electrophoretic profiles.

2. The method of claim 1, each repeat of step (4) comprising pushing each injected target/sample aliquot to a different starting point in the capillary prior to capillary electrophoresis, by pressure-injecting an aliquot of capillary electrophoresis running buffer into the capillary behind the injected target/sample aliquot, wherein the running buffer aliquot differs in amount for each repeat of step (4).

3. A method to detect, in a sample of complex biological material, any candidate hit compound that binds to a selected target at or above a selected binding strength and to determine a stability, during capillary electrophoresis, of any target/hit compound, complex detected, wherein the stability is determined to identify relative affinities of hit compounds, said method comprising, in the order given, the steps of:

(1) providing a predetermined concentration of a selected target;

(2) providing a sample of complex biological material;

(3) mixing the target with the sample to form a target/sample mixture and incubating the target/sample mixture;

(4) sequentially injecting multiple aliquots of the target/sample mixture into a capillary electrophoresis instrument comprising a capillary having a single detection point, such that the multiple target/sample aliquots are spaced apart along an axis of the capillary;

(5) subjecting the multiple target/sample aliquots within the capillary simultaneously to capillary electrophoresis, under conditions to detect any hit compound in the sample that binds to the target, so that a detectable amount of any complex formed in the multiple target/sample aliquots between the target and any candidate hit binding to the target at or above a selected binding strength of each target/sample aliquot undergoes a different capillary electrophoresis run time before reaching the detection point;

(6) tracking, at the detection point, a capillary electrophoretic migration of the target in each of the multiple target/sample aliquots, thereby generating different multiple capillary electrophoretic profiles of the target/sample aliquot at different capillary electrophoretic run times;

(7) determining whether at least one capillary electrophoretic profile of the target generated from step (6), when compared to a reference standard, indicates a presence of any bit compound(s) binding to the target; and (8) determining the stability, during capillary electrophoresis, of any target/hit compound complex (es) detected during step (6), by comparing the multiple capillary electrophoretic profiles.

4. The method of claim 3, step (4) further comprising pressure-injecting an aliquot of capillary electrophoresis running buffer into the capillary behind each injected target/sample aliquot, to place each injected target/sample aliquot at a different starting point in the capillary, prior to the capillary electrophoresis step.

5. The method of claim 3 or 4, wherein an aliquot of capillary electrophoresis running buffer is pressure-injected into the capillary immediately behind a last injected target/sample aliquot, prior to capillary electrophoresis, to push the last injected target/sample aliquot to a desired starting point in the capillary.

6. A method to detect, in a sample of complex biological material, any candidate hit compound that binds to a selected target at or above a selected binding strength and to determine a stability, during capillary electrophoresis, of any target/hit compound complex detected, wherein the stability is determined to identify relative affinities of hit compounds, said method comprising, in the order given, the steps of:

(1) providing a predetermined concentration of a selected target;

(2) providing a sample of complex biological material;

(3) mixing the target with the sample to form a target/sample mixture and incubating the target/sample mixture;

(4) injecting an aliquot of the target/sample mixture into a capillary electrophoresis instrument comprising a capillary having multiple detection points;

(5) subjecting the target/sample aliquot to capillary electrophoresis under conditions to detect a hit compound that binds to the target, wherein the conditions are optimized so that an amount is detected of any complex formed between the target and any candidate hit binding to the target at or above a selected binding strength;

(6) tracking a capillary electrophoretic migration of the target in the target/sample, aliquot at each of the multiple detection points, thereby generating different multiple capillary electrophoretic profiles of the target/sample aliquot at different capillary electrophoresis run times;

(7) determining whether at least one capillary electrophoretic profile of the target generated from step (6), when compared to a reference standard, indicates, a presence of any hit compound(s) binding to the target; and (8) determining the stability, during capillary electrophoresis, of any target/hit compound complex(es) detected, by comparing the multiple capillary electrophoretic profiles.

7. The method of claim 6, further comprising, between steps (4) and (5) injecting an aliquot of capillary electrophoresis running buffer into the capillary behind the injected target/sample aliquot to push the target/sample aliquot to a desired starting point in the capillary prior to capillary electrophoresis, and further comprising repeating step (4), the running buffer injection step, step (5), and step (6), one or more times prior to performing step (7), wherein a different amount of running buffer is injected in each repeat of the running buffer injection step.

8. The method of claim 6, further comprising, between steps (4) and (5), sequentially injecting one or more additional aliquots of the target/sample mixture into the capillary, such that the multiple target/sample aliquots are spaced apart along an axis of the capillary prior to capillary electrophoresis.

9. The method of claim 1, 3, or 6, wherein the reference standard comprises the capillary electrophoretic profile of the target without any target-binding ligand.

10. The method of claim 1, 3, or 6, wherein determining the stability, during capillary electrophoresis, of a detected target/hit compound complex comprises:

(a) determining whether each capillary electrophoretic profile generated from step (6), has any migration peak representing a target/hit compound complex and, if said migration peak is detected, proceeding to steps (b) and (c);

(b) measuring an area under each target/hit compound complex migration peak identified in step (a) for each capillary electrophoretic profile generated from step (6); and (c) using the measurements from step (b) to determine a rate at which each target/hit compound complex migration peak decreases as capillary electrophoresis run time increases for the target/sample aliquot.

11. The method of claim 1, 3, or 6, wherein a capillary electrophoresis running buffer includes a known, charged, weak-binding, competitive ligand to the target.

12. The method of claim 11, wherein the reference standard comprises the capillary electrophoretic profile of the target with the known competitive ligand and without any other target-binding ligand.

13. The method of claim 11, wherein determining the stability of a target/hit compound complex comprises:

(a) comparing at least one capillary electrophoretic profile, generated in step (6), to a reference standard comprising the capillary electrophoretic profile of the target with the known competitive ligand and without any other target-binding ligand;

(b) determining whether each capillary electrophoretic profile, generated from each performance of step (6), has migration peaks representing, respectively, a competitive ligand-shifted target and any target/hit compound complex;

(c) measuring an area under each migration peak identified in step (b), for each capillary electrophoretic profile generated from each performance of step (6); and (d) using the measurements from step (c) to determine the stability of any target/hit compound complex detected, by determining, as the capillary electrophoresis run time increases for the target/sample aliquot: a rate at which a competitive ligand-shifted target migration peak area increases, a rate at which a target/hit compound migration peak area decreases, or both.

14. The method of claim 1, 3, or 6, wherein the sample includes at least one hit compound that binds to the selected target.

15. The method of claim 1, 3, or 6, further comprising performing each of the recited steps on multiple samples, each sample comprising a different hit compound from each other, and ranking the hit compounds according to their respective binding strengths to the target, by comparing the stability, during capillary electrophoresis, of each target/hit compound complex detected.

16. The method of claim 1, 3, or 6, wherein the capillary electrophoresis conditions are optimized to detect a strong-binding hit compound having a dissociation constant ($K_D$) of less than about 10 nM and an off-rate ($K_{off}$) of less than about 0.01 ($s^{-1}$), which forms a target/hit complex whose capillary electrophoretic migration peak area decreases by no more than 50% after 1.5–5.0 minutes of capillary electrophoresis.

17. The method of claim 1, 3, or 6, wherein the capillary electrophoresis conditions are optimized to detect a moderate or stronger binding hit compound having a dissociation constant ($K_D$) of about 10.0 $\mu$M or less and an off-rate ($K_{off}$) of about 1.0 ($s^{-1}$) or less, which forms a target/hit complex whose capillary electrophoretic migration peak area decreases by 51–90% after 1.5–5.0 minutes of capillary electrophoresis.

18. The method of claim 1, 3, or 6, wherein the capillary electrophoresis conditions are optimized to detect a weak-binding or stronger hit compound having a dissociation constant ($K_D$) of greater than about 10 $\mu$M and an off-rate ($K_{off}$) of greater than about 1.0 ($s^{-1}$), which forms a target/hit compound complex whose capillary electrophoretic migration peak area decreases by 91–99% after 1.5–5.0 minutes of capillary electrophoresis.

19. The method of 1, 3, or 6, for detecting strong-binding hit compounds that are present with moderate or weaker binding hit compounds, wherein the capillary electrophoretic conditions are optimized so that strong-binding hit compound/target complexes remain substantially, intact while moderate-to-weak binding hit compound/target complexes largely dissociate during capillary electrophoresis.

20. The method of claim 19, wherein capillary electrophoresis is performed using at least one condition selected from the group consisting of: a capillary electrophoresis temperature within a range of about 20–45° C.; a capillary electrophoresis run time within a range of about 2.5–10.0 minutes; a capillary electrophoresis voltage within a range of about 5–30 kV; a capillary electrophoresis buffer having a pH within a range of about 3–10; and a capillary electrophoresis buffer having a salt concentration within a range of about 0–100 mM.

21. The method of claim 1, 3, or 6, for detecting moderate or stronger binding hit compounds that are present with weaker binding hit compounds, wherein the capillary electrophoretic conditions are optimized so that, moderate-to-strong-binding hit compound/target complexes remain substantially intact while weak-binding hit compound/target complexes largely dissociate during capillary electrophoresis.

22. The method of claim 21, wherein capillary electrophoresis is performed using at least one condition selected from the group consisting of: a capillary electrophoresis temperature within a range of about 5–25° C.; a capillary electrophoresis run time within a range of about 1.0–3.0 minutes; a capillary electrophoresis voltage within a range of about 5–30 kV; a capillary electrophoresis buffer having a pH within a range of about 3–10; and a capillary electrophoresis buffer having a salt concentration within a range of about 0–100 MM.

23. The method of claim 1, 3, or 6, wherein capillary electrophoresis is performed within a temperature range of about 4–45° C.

24. The method of claim 1, 3, or 6, wherein the capillary has a length within a range of about 0.5–100 cm.

25. The method of claim 1, 3, or 6, wherein the complex biological material is a member selected from the group consisting of: a naturally occurring product; a natural extract; a biological preparation; a chemical mixture; a pure compound library; and a combinatorial library.

26. The method of claim 11, wherein said known, weak-binding competitive ligand is selected from the group consisting of natural compounds, synthetic compounds, antibodies, and drugs known to bind to the target of interest.

27. The method of claim 1, 3, or 6, further comprising, when a candidate hit compound is present:

fractionating the complex biological material into multiple fractions, performing the steps recited in claim 1, 3, or 6, on each of the multiple fractions, and determining which fraction contains the candidate hit compound.

28. The method of claim 1, 3, or 6, further comprising:

isolating the candidate hit compound from the complex biological material, determining whether the isolated hit compound has not been previously identified as interacting with the target, and testing the isolated hit compound for therapeutic efficacy or pharmacokinetics properties against the target.

* * * * *

UNITED STATES PATENT AND TRADEMARK OFFICE
CERTIFICATE OF CORRECTION

PATENT NO. : 6,524,866 B1
DATED : February 25, 2003
INVENTOR(S) : Dallas E. Hughes et al.

It is certified that error appears in the above-identified patent and that said Letters Patent is hereby corrected as shown below:

Column 5,
Line 67, "(step 5 of the above-described method)," should read -- (step 5), --;

Column 6,
Line 1, "(step 5 of the above-described method)," should read -- (step 5), --;

Column 10,
Line 12, "to to" should read -- to --;

Column 11,
Line 43, "($k_{off}$)" should read -- ($K_{off}$) --;

Column 15,
Line 31, "conditions for" should read -- conditions optimized for --;
Line 47, "indicates a" should read -- indicates the --;
Line 64, "a stability" should read -- the stability --;
Line 66, "identify relative" should read -- identify the relative --;

Column 16,
Line 14, "conditions to" should read -- conditions optimized to --;
Line 30, "indicates a" should read -- indicates the --;
Line 31, "bit" should read -- hit --;
Line 54, "identify relative" should read -- identify the relative --;
Line 66, "conditions to" should read -- conditions optimized to --;

Column 17,
Line 13, "indicates, a" should read -- indicates the --;
Line 34, "an axis of" should read -- the axis of --; and

UNITED STATES PATENT AND TRADEMARK OFFICE
CERTIFICATE OF CORRECTION

PATENT NO. : 6,524,866 B1
DATED : February 25, 2003
INVENTOR(S) : Dallas E. Hughes et al.

It is certified that error appears in the above-identified patent and that said Letters Patent is hereby corrected as shown below:

Column 18,
Line 51, "of 1" should read -- of claim 1 --.

Signed and Sealed this

Second Day of November, 2004

JON W. DUDAS
*Director of the United States Patent and Trademark Office*